United States Patent [19]

Axen et al.

[11] 4,312,810

[45] Jan. 26, 1982

[54] 2,5-INTER-O-PHENYLENE-3,4-DINOR-5,9α-EPOXY-9-DEOXY-PGF$_1$ COMPOUNDS

[75] Inventors: Udo F. Axen, Plainwell; John C. Sih, Kalamazoo Township, Kalamazoo County, both of Mich.

[73] Assignee: The Upjohn Company, Kalamazoo, Mich.

[21] Appl. No.: 62,443

[22] Filed: Jul. 31, 1979

Related U.S. Application Data

[63] Continuation-in-part of Ser. No. 962,845, Nov. 22, 1978, abandoned.

[51] Int. Cl.$^3$ ............................................. C07D 311/02
[52] U.S. Cl. ........................... 260/345.2; 260/326.36; 260/326.5 D; 260/346.22; 260/346.73; 544/151; 544/153; 544/376; 546/196; 542/426; 542/429; 424/273 R
[58] Field of Search ..................... 260/345.2; 542/426, 542/429

[56] References Cited

U.S. PATENT DOCUMENTS

| | | | |
|---|---|---|---|
| 3,728,382 | 4/1973 | Bundy | 260/501.15 |
| 3,903,131 | 9/1975 | Magerlein | 260/468 D |
| 3,962,293 | 6/1976 | Magerlein | 260/408 |
| 4,026,909 | 5/1977 | Yankee | 260/408 |
| 4,029,681 | 6/1977 | Smith | 260/408 |
| 4,123,441 | 10/1978 | Johnson | 260/345.2 |
| 4,138,575 | 2/1979 | Bundy et al. | 560/55 |

Primary Examiner—Nicky Chan
Attorney, Agent, or Firm—Robert A. Armitage

[57] ABSTRACT

This invention relates to certain structural and pharmacological analogs of prostacyclin (PGI$_2$) and 5,6-dehydroprostacyclin (PGI$_1$) and 5,9α-epoxy-9-deoxy-PGF$_1$, wherein between the position beta to the carboxy (C-2) and C-5 there is substituted an inter-o-phenylene for the ethylene chain. These novel 2,5-inter-o-phenylene-3,4-dinor-prostaglandin or prostacyclin-type compounds are useful for certain of the same pharmacological purposes as prostacyclin, particularly being smooth muscle stimulators, blood pressure depressors and platelet aggregation inhibitors. Also provided are novel intermediates therefor, namely corresponding interphenylene-containing PGF$_{2α}$ and 5-halo-PGI$_1$ and 6-halo-5,9α-epoxy-9-deoxy-PGF$_1$ compounds.

45 Claims, No Drawings

2,5-INTER-O-PHENYLENE-3,4-DINOR-5,9α-EPOXY-9-DEOXY-PGF₁ COMPOUNDS

The present application is a continuation-in-part of Ser. No. 962,845, filed 22 Nov. 1978, now abandoned.

The present invention relates to prostacyclin analogs, the preparation and use of which is hereby incorporated by reference from that portion of U.S. Pat. No. 4,281,113 identified as APPENDIX A (Column 3, line 42, through Columns 33-34, line 15).

We claim:

1. A prostacyclin analog of formula X

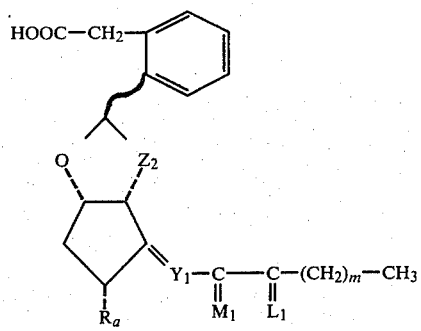

wherein $Z_2$ is cis-CH=CH— or —CH$_2$CH$_2$—;
wherein $R_8$ is hydrogen, hydroxy, or hydroxymethyl;
wherein $Y_1$ is
 (1) trans-CH=CH—,
 (2) cis-CH=CH—,
 (3) —CH$_2$CH$_2$—, or
 (4) —C≡C—;
wherein $M_1$ is α-$R_5$:β-OH or α-OH:β-$R_5$, where is $R_5$ is hydrogen or methyl;
wherein $L_1$ is α-$R_3$:β-$R_4$, α-$R_4$:β-$R_3$, or a mixture of α-$R_3$:β-$R_4$ and α-$R_4$:β-$R_3$, wherein $R_3$ and $R_4$ are hydrogen, methyl, or fluoro, being the same or different, with the proviso that one of $R_3$ and $R_4$ is fluoro only when the other is hydrogen or fluoro; wherein m is an integer from one to 5, inclusive; or a pharmacologically acceptable salt thereof.

2. A prostacyclin analog according to claim 1, wherein $R_8$ is hydroxymethyl.

3. 9,11-Dideoxy-11α-hydroxymethyl-2,5-inter-o-phenylene-3,4-dinor-6,7-didehydro-5,9α-epoxy-PGF₁, a prostacyclin analog according to claim 2.

4. A prostacyclin analog according to claim 1, wherein $R_8$ is hydrogen.

5. 9,11-Dideoxy-2,5-inter-o-phenylene-3,4-dinor-6,7-didehydro-5,9α-epoxy-PGF₁, a prostacyclin analog according to claim 4.

6. A prostacyclin analog according to claim 1, wherein $R_8$ is hydroxy.

7. A prostacyclin analog according to claim 6, wherein $Y_1$ is —C≡C—.

8. 13,14-Didehydro-2,5-inter-o-phenylene-3,4-dinor-6,7-didehydro-5,9α-epoxy-9-deoxy-PGF₁, a prostacyclin analog according to claim 7.

9. 15-Methyl-13,14-didehydro-2,5-inter-o-phenylene-3,4-dinor-6,7-didehydro-5,9α-epoxy-9-deoxy-PGF₁, a prostacyclin analog according to claim 7.

10. 16,16-Dimethyl-13,14-didehydro-2,5-inter-o-phenylene-3,4-dinor-6,7-didehydro-5,9α-epoxy-9-deoxy-PGF₁, a prostacyclin analog according to claim 7.

11. 16,16-Difluoro-15-methyl-13,14-didehydro-2,5-inter-o-phenylene-3,4-dinor-6,7-didehydro-5,9α-epoxy-9-deoxy-PGF₁, a prostacyclin analog according to claim 7.

12. A prostacyclin analog according to claim 6, wherein $Y_1$ is cis-CH=CH—.

13. cis-13-2,5-Inter-o-phenylene-3,4-dinor-6,7-didehydro-5,9α-epoxy-9-deoxy-PGF₁, a prostacyclin analog according to claim 12.

14. A prostacyclin analog according to claim 6, wherein $Y_1$ is —CH$_2$CH$_2$—.

15. 13,14-Dihydro-2,5-inter-o-phenylene-3,4-dinor-6,7-didehydro-5,9α-epoxy-9-deoxy-PGF₁, a prostacyclin analog according to claim 14.

16. 13,14-Dihydro-16,16-dimethyl-2,5-inter-o-phenylene-3,4-dinor-6,7-didehydro-5,9α-epoxy-9-deoxy-PGF₁, a prostacyclin analog according to claim 14.

17. 13,14-Dihydro-15,16,16-trimethyl-2,5-inter-o-phenylene-3,4-dinor-6,7-didehydro-5,9α-epoxy-9-deoxy-PGF₁, a prostacyclin analog according to claim 14.

18. 13,14-Dihydro-16,16-difluoro-2,5-inter-o-phenylene-3,4-dinor-6,7-didehydro-5,9α-epoxy-9-deoxy-PGF₁, a prostacyclin analog according to claim 14.

19. A prostacyclin analog according to claim 6, wherein $Y_1$ is trans-CH=CH—.

20. A prostacyclin analog according to claim 19, wherein $Z_2$ is —CH$_2$CH$_2$—.

21. A prostacyclin analog according to claim 20, wherein m is 3.

22. A prostacyclin analog according to claim 21, wherein $R_5$ is methyl.

23. 15-Methyl-2,5-inter-o-phenylene-3,4-dinor-5,9α-epoxy-9-deoxy-PGF₁, a prostacyclin analog according to claim 22.

24. A prostacyclin analog according to claim 21, wherein $R_5$ is hydrogen.

25. A prostacyclin analog according to claim 24, wherein at least one of $R_3$ and $R_4$ is fluoro.

26. 16,16-Difluoro-2,5-inter-o-phenylene-3,4-dinor-5,9α-epoxy-9-deoxy-PGF₁, a prostacyclin analog according to claim 25.

27. A prostacyclin analog according to claim 24, wherein at least one of $R_3$ and $R_4$ is methyl.

28. 16,16-Dimethyl-2,5-inter-o-phenylene-3,4-dinor-5,9α-epoxy-9-deoxy-PGF₁, a prostacyclin analog according to claim 27.

29. A prostacyclin analog according to claim 24, wherein $R_3$ and $R_4$ are both hydrogen.

30. 2,5-Inter-o-phenylene-3,4-dinor-5,9α-epoxy-9-deoxy-PGF₁, tris(hydroxymethyl)aminomethane salt, a prostacyclin analog according to claim 29.

31. 2,5-Inter-o-phenylene-3,4-dinor-5,9α-epoxy-9-deoxy-PGF₁, adamantanamine salt, a prostacyclin analog according to claim 29.

32. 2,5-Inter-o-phenylene-3,4-dinor-5,9α-epoxy-9-deoxy-PGF₁, a prostacyclin analog according to claim 29.

33. A prostacyclin analog according to claim 19, wherein $Z_2$ is cis-CH=CH—.

34. A prostacyclin analog according to claim 33, wherein m is 3.

35. A prostacyclin analog according to claim 34, wherein $R_5$ is methyl.

36. 15-Methyl-2,5-inter-o-phenylene-3,4-dinor-6,7-didehydro-5,9α-epoxy-9-deoxy-PGF₁, a prostacyclin analog according to claim 35.

37. A prostacyclin analog according to claim 34, wherein $R_5$ is hydrogen.

38. A prostacyclin analog according to claim 37, wherein at least one of $R_3$ and $R_4$ is fluoro.

39. 16,16-Difluoro-2,5-inter-o-phenylene-3,4-dinor-6,7-didehydro-5,9α-epoxy-9-deoxy-PGF$_1$, a prostacyclin analog according to claim 38.

40. A prostacyclin analog according to claim 37, wherein at least one of $R_3$ and $R_4$ is methyl.

41. 16,16-Dimethyl-2,5-inter-o-phenylene-3,4-dinor-6,7-didehydro-5,9α-epoxy-9-deoxy-PGF$_1$, a prostacyclin analog according to claim 40.

42. A prostacyclin analog according to claim 37, wherein $R_3$ and $R_4$ are both hydrogen.

43. 2,5-Inter-o-phenylene-3,4-dinor-6,7-didehydro-5,9α-epoxy-9-deoxy-PGF$_1$, tris(hydroxymethyl)aminomethane salt, a prostacyclin analog according to claim 42.

44. 2,5-Inter-o-phenylene-3,4-dinor-6,7-didehydro-5,9α-epoxy-9-deoxy-PGF$_1$, adamantanamine salt, a prostacyclin analog according to claim 42.

45. 2,5-Inter-o-phenylene-3,4-dinor-6,7-didehydro-5,9α-epoxy-9-deoxy-PGF$_1$, a prostacyclin analog according to claim 42.

* * * * *

UNITED STATES PATENT OFFICE
CERTIFICATE OF CORRECTION

Patent No. 4,312,810        Dated 1-26-82

Inventor(s) Axen, U.F. and Sih, J.C.

It is certified that error appears in the above-identified patent and that said Letters Patent are hereby corrected as shown below:

Column 1, lines 25-28

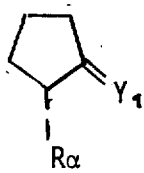   should appear as   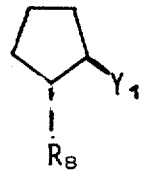

Column 1, line 37 reads --whereis $R_5$ is-- should read --wherein $R_5$ is--

Signed and Sealed this

Fourteenth Day of September 1982

[SEAL]

Attest:

Attesting Officer

GERALD J. MOSSINGHOFF
Commissioner of Patents and Trademarks